(12) United States Patent
Taylor

(10) Patent No.: US 8,118,839 B2
(45) Date of Patent: Feb. 21, 2012

(54) INTERSPINOUS IMPLANT

(75) Inventor: Jean Taylor, Cannes (FR)

(73) Assignee: Kyphon Sarl, Neuchatel (CH)

( * ) Notice: Subject to any disclaimer, the term of this patent is extended or adjusted under 35 U.S.C. 154(b) by 297 days.

(21) Appl. No.: 12/513,100

(22) PCT Filed: Nov. 7, 2007

(86) PCT No.: PCT/IB2007/003389
§ 371 (c)(1),
(2), (4) Date: May 19, 2009

(87) PCT Pub. No.: WO2008/056237
PCT Pub. Date: May 15, 2008

(65) Prior Publication Data
US 2010/0070038 A1    Mar. 18, 2010

Related U.S. Application Data

(60) Provisional application No. 60/857,589, filed on Nov. 8, 2006.

(30) Foreign Application Priority Data

Nov. 8, 2006 (FR) ..................................... 06 09738

(51) Int. Cl.
*A61B 17/70* (2006.01)
*A61F 2/44* (2006.01)

(52) U.S. Cl. ....................... 606/248; 606/249; 623/17.16

(58) Field of Classification Search .................. None
See application file for complete search history.

(56) References Cited

U.S. PATENT DOCUMENTS 624,969 A    5/1899    Peterson
1,153,797 A    9/1915    Kegreisz
1,516,347 A    11/1924    Pataky
1,870,942 A    8/1932    Beatty
2,077,804 A    4/1937    Morrison
2,299,308 A    10/1942    Creighton
2,485,531 A    10/1949    Dzus et al.
2,607,370 A    8/1952    Anderson
2,677,369 A    5/1954    Knowles
2,685,877 A    8/1954    Dobelle
3,065,659 A    11/1962    Eriksson et al.
3,108,595 A    10/1963    Overment (Continued)

FOREIGN PATENT DOCUMENTS

DE    2821678 A1    11/1979

(Continued)

OTHER PUBLICATIONS

"Dispositivo Intervertebrale Ammortizzante DIAM," date unknown, p. 1.

(Continued)

*Primary Examiner* — David H Willse
*Assistant Examiner* — Javier Blanco

(57) ABSTRACT

This interspinous implant is able to be engaged between the spinal processes of two vertebrae and formed by a block of elastically deformable material. According to the invention, the block is subdivided into a central part made from a first elastically deformable material and two lateral parts made from a second elastically deformable material, more rigid than the first material. The lateral parts are situated on the two opposite lateral sides of the central part, that is to say on the sides intended to be situated longitudinally on each side of the spinal processes after implantation, and being connected to the central part.

7 Claims, 1 Drawing Sheet

U.S. PATENT DOCUMENTS

| | | |
|---|---|---|
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,436,140 B1 | 8/2002 | Liu et al. |
| 6,440,169 B1 | 8/2002 | Elberg et al. |
| 6,447,513 B1 | 9/2002 | Griggs |
| 6,447,546 B1 | 9/2002 | Bramlet et al. |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |

| | | |
|---|---|---|
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartman et al. |
| 7,862,615 B2 | 1/2011 | Carli et al. |
| 7,901,430 B2 | 3/2011 | Matsuura et al. |
| 7,927,354 B2 | 4/2011 | Edidin et al. |
| 2001/0016743 A1 | 8/2001 | Zucherman et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2003/0176925 A1 | 9/2003 | Paponneau |
| 2004/0010312 A1 | 1/2004 | Enayati |
| 2004/0010316 A1 | 1/2004 | William et al. |
| 2004/0064094 A1 | 4/2004 | Freyman |
| 2004/0087947 A1 | 5/2004 | Lim et al. |
| 2004/0097931 A1 | 5/2004 | Mitchell |
| 2004/0106995 A1 | 6/2004 | LeCoudeic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0172029 A1 | 9/2004 | Lerch |
| 2004/0186577 A1 | 9/2004 | Ferree |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049590 A1 | 3/2005 | Alleyne et al. |
| 2005/0049708 A1 | 3/2005 | Atkinson et al. |
| 2005/0056292 A1 | 3/2005 | Cooper |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyer et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0049935 A1 | 3/2007 | Edidin et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0225810 A1 | 9/2007 | Colleran et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233084 A1 | 10/2007 | Betz et al. |
| 2007/0233089 A1 | 10/2007 | DiPoto et al. |
| 2007/0250060 A1 | 10/2007 | Anderson et al. |

| | | | |
|---|---|---|---|
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0270874 A1 | 11/2007 | Anderson | |
| 2007/0272259 A1 | 11/2007 | Allard et al. | |
| 2007/0276368 A1 | 11/2007 | Trieu et al. | |
| 2007/0276369 A1 | 11/2007 | Allard et al. | |
| 2007/0276493 A1 | 11/2007 | Malandain et al. | |
| 2007/0276496 A1 | 11/2007 | Lange et al. | |
| 2007/0276497 A1 | 11/2007 | Anderson | |
| 2007/0282443 A1 | 12/2007 | Globerman et al. | |
| 2008/0021457 A1 | 1/2008 | Anderson et al. | |
| 2008/0021460 A1 | 1/2008 | Bruneau et al. | |
| 2008/0058934 A1 | 3/2008 | Malandain et al. | |
| 2008/0097446 A1 | 4/2008 | Reiley et al. | |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0177306 A1 | 7/2008 | Lamborne et al. | |
| 2008/0183209 A1 | 7/2008 | Robinson et al. | |
| 2008/0183211 A1 | 7/2008 | Lamborne et al. | |
| 2008/0183218 A1 | 7/2008 | Mueller et al. | |
| 2008/0195152 A1 | 8/2008 | Altarac et al. | |
| 2008/0215094 A1 | 9/2008 | Taylor | |
| 2008/0221685 A9 | 9/2008 | Altarac et al. | |
| 2008/0234824 A1 | 9/2008 | Youssef et al. | |
| 2008/0262617 A1 | 10/2008 | Froehlich et al. | |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0099610 A1 | 4/2009 | Johnson et al. | |
| 2009/0105766 A1 | 4/2009 | Thompson et al. | |
| 2009/0105773 A1 | 4/2009 | Lange et al. | |
| 2009/0234389 A1 | 9/2009 | Chuang et al. | |
| 2009/0240283 A1 | 9/2009 | Carls et al. | |
| 2009/0270918 A1 | 10/2009 | Attia et al. | |
| 2009/0292316 A1 | 11/2009 | Hess | |
| 2009/0326538 A1 | 12/2009 | Sennett et al. | |
| 2010/0121379 A1 | 5/2010 | Edmond | |
| 2010/0191241 A1 | 7/2010 | McCormack et al. | |
| 2010/0204732 A1 | 8/2010 | Aschmann et al. | |
| 2010/0211101 A1 | 8/2010 | Blackwell et al. | |

FOREIGN PATENT DOCUMENTS

| | | |
|---|---|---|
| DE | 3922044 A1 | 2/1991 |
| DE | 4012622 C1 | 7/1991 |
| DE | 202006018978 U1 | 2/2007 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | 2006106246 A2 | 10/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Discord Tech., 2006, vol. 00, No. 00, pp. 1-7.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Kramer et al., "Interveterbral Disk Diseases: Causes, Diagnosis, Treatment and Prophylaxis," pp. 244-249, Medical, 1990.

Phillips et al., "Biomechanics of Posterior Dynamic Stabling Device (DIAM) After Facetectomy and Disectomy," The Spine Journal, 2006, vol. 6, pp. 714-722.

Taylor et al., "Device for Intervertebral Assisted Motion: Technique and Intial Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Zdeblick et al., "Two-Point Fixation of the Lumbar Spine Differential Stability in Rotation," Spine, 1991, pp. S298-S301, vol. 16, No. 6, Supplement.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

INTERSPINOUS IMPLANT

This application claims the benefit of French Application No. 06/09738 filed Nov. 8, 2006 and U.S. Application No. 60/857,589 filed Nov. 8, 2006.

The present invention concerns an interspinous implant.

It is known, through the document WO 99/42051 in the name of the applicant, how to produce an elastically deformable interspinous implant able to damp the posterior movement of the vertebrae during extension of the spinal column. This implant is substantially in the shape of an H, that is to say it comprises a pair of projecting top arms and a pair of projecting bottom arms, delimiting respective top and bottom recesses able to receive the spinal processes of the two vertebrae; it is formed from a block of deformable viscoelastic material, in particular silicone, possibly contained in an envelope of woven material, in particular polyester.

This implant gives satisfaction in practice, constituting an alternative to the other methods of surgical treatment of vertebrae, which are more invasive, in particular the methods of interpedicular osteosynthesis consisting of fitting a rigid material with pedicular screws and connecting rods, joining the treated vertebrae.

It appears however that, in certain cases, in particular in the case of strong patients or those having a local compensatory hyperlordosis, the existing implant has insufficient damping capacity. In such patients fitting the largest implant existing in the range of implants available is not a satisfactory solution since there is a risk of producing an excessively great distraction, leading to excessive pressure, in particular anterior, on the intervertebral disc.

Moreover, it appears that the holding of the implant in position may not always be perfectly guaranteed, in particular during longitudinal torsion movements of the spinal column or lateral bending movements thereof. This risk is partially attenuated by means of ligaments engaged through the interspinous middle part of the implant and around the spinal processes, which makes the fitting of the implant more invasive.

The document WO 2006/106246 describes an implant comprising two distinct rigid pieces, and means for the mutual association of these pieces in rotation, forming a swivel. The existence of such rigid pieces on such an implant is not desirable because of the risks that this may present in the event of wear and/or movement of the implant. This implant is not affected by the aforementioned technical problems posed on an implant consisting of a block of deformable material, namely the problem of insufficient damping capacity in certain cases and the problem of a holding in position that is not perfectly guaranteed.

The document US 2005/203512 describes an interspinous implant comprising an interspinous central part made from high molecular weight polyethylene or PEEK, that is to say rigid materials, and projecting arms made from shape-memory metal. In particular, the projecting arms situated on the same side are formed by the same blade made from shape-memory metal, passing through the interspinous part of the implant.

The same comments as above can be made concerning the implant according to this prior document.

The present invention aims to remedy the aforementioned problems posed with an implant formed by a block of deformable material.

The implant concerned is, as known per se, suitable for being engaged between the spinal processes of two vertebrae and is formed by a block of elastically deformable material.

According to the invention, the said block is subdivided into a central part made from a first elastically deformable material and two lateral parts made from a second elastically deformable material, more rigid than said first material, said lateral parts being situated on the two opposite lateral sides of the central part, that is to say on the sides intended to be situated longitudinally on each side of the spinal processes after implantation, and being connected to said central part.

The inventor in fact found that the insufficient damping capacity of the existing implant resulted, in certain clinical anatomical situations, from a lateral creep of the material of the implant under the effect of said compression forces. In the implant according to the invention, said lateral parts made from a more rigid material oppose this risk of lateral creep of the material constituting said central part of the block.

Preferably, the two lateral parts made from a more rigid material are connected to each other through the interspinous middle portion of the implant, by a connecting part.

This connecting part makes it possible, in addition to the inherent rigidity of said lateral parts made from more rigid material, to perfectly oppose the aforementioned lateral creep of said central part of the implant.

Said connecting part is preferably produced from the same material as the two lateral parts made from more rigid material.

Said connecting part can be tubular, in order to allow where necessary the passage of one or more ligaments through the implant, which provide additional holding of the implant with respect to the vertebrae. The connecting part can also be solid in transverse section, then increasing the degree of damping of the interspinous part of the implant.

The implant can have a parallelepipedal or cylindrical shape, in which case the resistance to lateral creep of the central part of the implant is obtained by connecting said lateral parts made from more rigid material through the middle portion of the implant. Preferably, however, the implant according to the invention has an H shape, that is to say comprises a pair of projecting top arms and a pair of projecting bottom arms, delimiting respective top and bottom recesses able to receive the spinal processes of the two vertebrae, and said lateral parts made from a more rigid material extend at least over part of the height of at least one of said projecting branches.

Said lateral parts made from a more rigid material have in this case the advantage of reinforcing the rigidity of one or more of said projecting arms and therefore increasing the stability and consequently increasing the degree of holding in position of the implant after fitting, in particular in the case of twisting movements of the vertical column or lateral bending thereof. The inventor found that the aforementioned risk of movement of the implant according to the prior art resulted from insufficient rigidity of the projecting arms of this implant, in particular in the case of significant lateral creep of the material of the implant. Said lateral parts made from a more rigid material according to the invention make it possible to solve this problem.

These lateral parts made from a more rigid material preferably extend over the whole of the height of said projecting arms. The rigidity of said second material constituting these lateral parts can then be sufficient to ensure the aforementioned lateral restraint of the central part of the implant with regard to the creep of the material constituting said block. These same lateral parts can also be connected to each other through the interspinous middle portion of the implant, by a connecting part.

Said lateral parts made from a more rigid material preferably closely bonded to the elastically deformable material forming the central part of the implant, over the whole of the assembly interface of each lateral part with this central part. This connection over the whole of this interface helps to oppose the lateral creep of the material of the central part given that the sliding of one assembly face with respect to the other is prevented.

The implant can, in this case, be obtained by moulding said lateral parts made from a more rigid material on said central part or, when there is a connection of said lateral parts made from more rigid material with each other at the interspinous middle part, by moulding said central part on said lateral parts made from more rigid material and on the part forming said connection.

When the implant has an H shape, at least one of said lateral parts made from more rigid material can have a reduced thickness at the interspinous middle portion of the implant, so as to allow bending of the corresponding top and bottom projecting arms one towards the other, in order to make possible lateral insertion of the implant in the interspinous space.

Such a possibility of lateral insertion is advantageous given that it preserves the integrity of the ligamentary system better than a posterior insertion.

Said first material can in particular be a viscoelastic material. This material may have variable rigidity, increasing as the degree of compression undergone by this material increases.

Said first material can in particular be a silicone, with a hardness for example of 65 Shore A.

Said second material has a higher hardness than that of the first material. It may for example be a silicone with a hardness of around 85 shore A.

The implant can be contained in a sheath made from textile material, in particular polyester.

The invention will be clearly understood and other characteristics and advantages thereof will emerge with reference to the accompany schematic drawing showing, by way of non-limitative examples, several possible embodiments of the implant that it concerns.

For simplification, the parts or elements of one embodiment that are found again in an identical or similar manner in another embodiment will be identified by the same numerical references and will not be described again.

Figure 1:
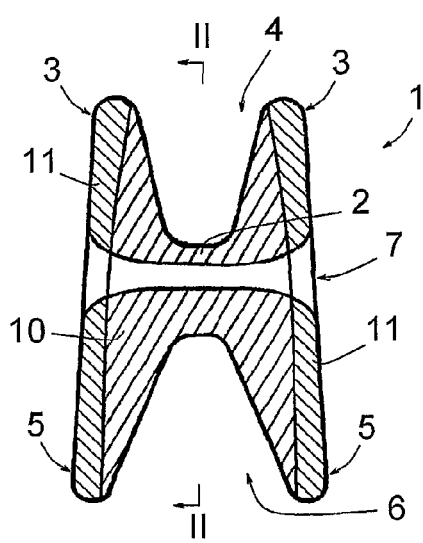
FIG. 1 is a view in section of it along the line I-I in FIG. 2, according to a first embodiment.
Figure 2:
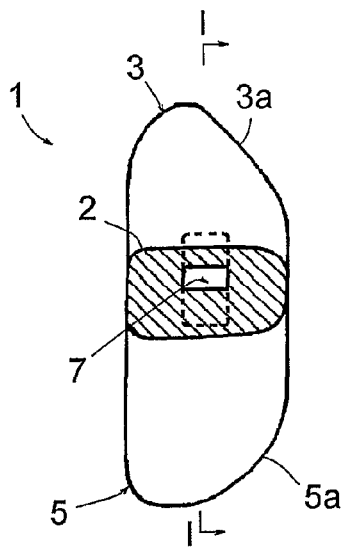
FIG. 2 is a view in section of it along the line II-II in FIG. 1.

FIGS. 1 and 2 show an interspinous implant 1 suitable for being inserted between the spinal processes of two vertebrae so as to be able to damp the posterior movement of these vertebrae during extension of the spinal column. The implant 1 is substantially in an H shape, that is to say comprises a middle part 2 intended to be placed between said spinal processes, a pair of projecting top arms 3 delimiting a top recess 4, and a pair of projecting bottom arms 5 delimiting a bottom recess 6, these recesses 4 and 6 being able to receive the spinal processes of the two vertebrae.

As shown by FIG. 2, the arms 3 and 5 have truncated anterior top edges 3a, 5a, respectively inclined and rounded, so that the implant 1 can be fitted at the base of the spinal processes of the vertebrae, as close as possible to the lamellae.

The implant 1 also comprises a conduit 7 formed through the part 2, the ends of which are splayed. This conduit 7 serves if necessary for fitting ligaments engaged through it and around the spinal processes of the two vertebrae.

The implant 1 can comprise an envelope made from woven material, in particular polyester, which covers it entirely.

As shown, the implant 1 is formed from parts made from different materials, namely:
  a central part 10 made from a first elastically deformable material, for example a silicone with a hardness of 65 Shore A, and
  two lateral parts 11 made from a second elastically deformable material, more rigid than said first material, situated on the two opposite lateral sides of the central part 10, that is to say on the sides intended to be situated longitudinally on each side of the spinal processes after implantation, these lateral parts 11 being connected to the central part 10.

The lateral parts 11 extend over the whole of the height of the implant 1; they have, in the embodiment shown in FIG. 1, a thickness varying little but slightly greater at the free ends of the arms 3 and 5, and are closely bonded to the central part 10 over the whole of the assembly interface with this central part. They can in particular be made from silicone with a higher Shore A hardness than that of the material of the central part 10, for example around 85 Shore A, and be moulded onto this central part 10.

These more rigid lateral parts 11 oppose a risk of lateral creep of the material constituting the central part 10 under the effect of high compression forces liable to be exerted on the part 2 by the spinal processes and therefore preserve sufficient damping capacity for this part 2.

The lateral parts 11 also have the result of reinforcing the rigidity of the arms 3 and 5 and therefore increasing the degree of holding of the implant 1 in position after fitting, in particular in the case of twisting movements of the vertebral column or lateral bending thereof, and particularly in the case of significant compression of the part 2.

Figure 3:
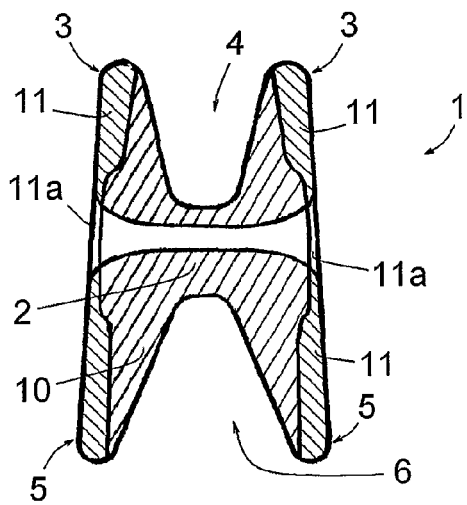
FIG. 3 is a view of it similar to FIG. 1, according to a second embodiment.
Figure 4:
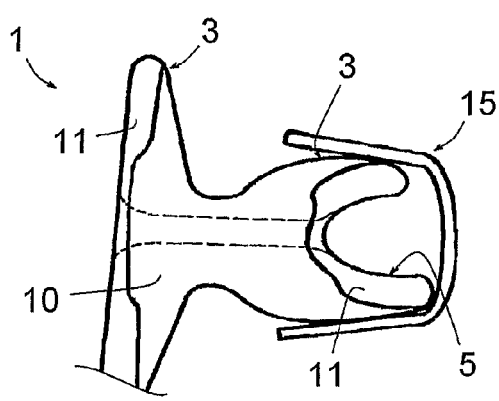
FIG. 4 is a view of it according to this second embodiment, in an implantation configuration.

FIG. 3 shows that the lateral parts 11 can have a portion 11a of reduced thickness at the interspinous middle portion of the implant 1, so as to allow, as shown by FIG. 4, bending towards each other of the arms 3 and 5 situated on the same side of the implant 1, in order to make possible a lateral insertion of the implant in the interspinous space. The arms 3 and 5 can be held in this flexed position by means of a holding link 15.

Figure 5:
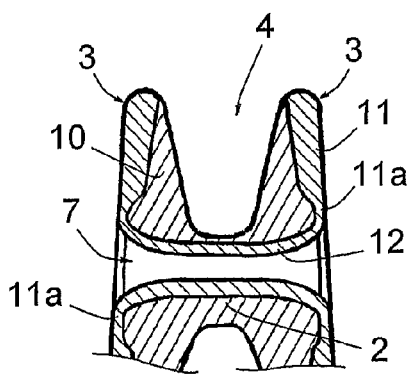
FIG. 5 is a view of it similar to FIG. 1, according to a third embodiment.

FIG. 5 shows that the lateral parts 11 can also be connected to each other through the part 2 of the implant 1. The latter then comprises an element consisting of the two parts 11 and the middle connecting part 12, on which the central part 10 is overmoulded.

In this case, the connecting part 12 is tubular, in order to allow where necessary the passage of one or more ligaments through it affording additional holding of the implant 1 with respect to the vertebrae.

Figure 6:
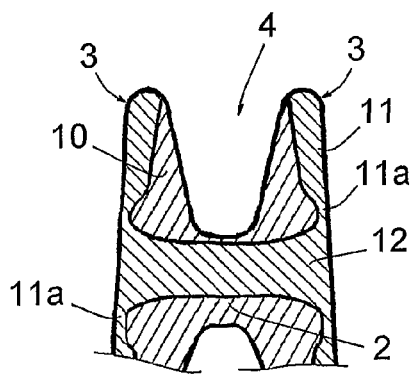
FIG. 6 is a view of it similar to FIG. 1, according to a fourth embodiment.

FIG. 6 shows that the connecting part 12 can also be solid in transverse section, then increasing the degree of damping of the interspinous part of the implant 1.

As is clear from the above, the invention provides an interspinous implant formed by a block of elastically deformable material, having in all cases sufficient damping capacity, in particular in the case of strong patients or those having local compensatory hyperlordosis, and the holding in place of which is reinforced, which may make unnecessary the fitting of ligaments around the spinal processes of the vertebrae treated.

It goes without saying that the invention is not limited to the embodiment described above by way of example but extends to all embodiments covered by the accompanying claims.

The invention claimed is:

1. An interspinous implant for implantation between two adjacent spinous processes, comprising:
   first and second arms forming a concave recess configured to receive one of the adjacent spinous processes;
   an inner central portion made from a first elastically deformable material, the inner central portion having:
      first and second outboard surfaces facing in opposite directions from one another;
      first and second inboard surfaces facing each other and forming at least part of the first and second arms respectively;
      an upper surface forming at least part of the concave recess;
   first and second outer lateral portions made from a second elastically deformable material more rigid than said first elastically deformable material, said first and second lateral portions being situated on opposite lateral sides of the first and second outboard surfaces of the inner central portion and adapted to be located along each side of the spinous processes after implantation, wherein the first and second outer lateral portions form at least part of the first and second arms respectively;
   wherein the first and second arms each have respective heights, and wherein said second elastically deformable material of the first and second outer lateral portions extends over a portion of the height of at least one of the first and second arms;
   wherein the concave recess is a first concave recess and the inner central portion is a first inner central portion and wherein the implant further comprises:
   third and fourth arms forming a second concave recess configured to receive the other of the adjacent spinous processes;
   a second inner central portion made from the first elastically deformable material; the second central portion having:
      first and second outboard surfaces facing in opposite directions from one another;
      first and second inboard surfaces facing each other and forming at least part of the third and fourth arms respectively;
   third and fourth outer lateral portions made from the second elastically deformable material, the third and fourth lateral portions being situated on opposing lateral sides of the first and second outboard surfaces of the second inner central portion, wherein the third and fourth lateral portions form at least part of the third and fourth arms respectively;
   wherein at least one of the first and second lateral portions and at least one of the third and fourth lateral portions has a reduced thickness portion so as to allow bending of the corresponding arms on the same side of the implant towards each other.

2. The implant of claim 1 wherein a connecting part located adjacent to the central portion connects the first and second outer lateral portions.

3. The implant of claim 2 wherein the connecting part is made from the second elastically deformable material.

4. The implant of claim 2 wherein the connecting part has a solid transverse section.

5. The implant of claim 1 wherein the second elastically deformable material of one of the first and second outer lateral portions extends over the entire height of one of the arms.

6. The implant of claim 5 wherein a connecting portion located adjacent to the central portion connects the first and second outer lateral portions.

7. The implant of claim 1 wherein the central portion and said lateral portions are produced from silicone.

* * * * *